United States Patent [19]

Damke et al.

[11] 4,353,510
[45] Oct. 12, 1982

[54] SPOOL BODY FOR HOLDING A PLASTER BANDAGE

[75] Inventors: Otto Damke, Neuwied; Hubert F. Reutter, St. Augustin, both of Fed. Rep. of Germany

[73] Assignee: Lohmann GmbH & Co. KG, Neuwied, Fed. Rep. of Germany

[21] Appl. No.: 200,485

[22] Filed: Oct. 24, 1980

[30] Foreign Application Priority Data

Oct. 26, 1979 [DE] Fed. Rep. of Germany ... 7930408[U]

[51] Int. Cl.³ ..................... B65H 75/10; B65H 75/12
[52] U.S. Cl. .............................................. 242/118.32
[58] Field of Search ............. 242/118.1, 118.2, 118.32, 242/60; 68/189, 198; 128/155, 156, 169, 170

[56] References Cited

U.S. PATENT DOCUMENTS 2,162,841  6/1939  Dunlap ...................... 242/118.1
3,643,888  2/1972  Blue .......................... 242/118.32
3,756,532  9/1973  Draper ....................... 242/118.11

Primary Examiner—Leonard D. Christian
Attorney, Agent, or Firm—Becker & Becker, Inc.

[57] ABSTRACT

A cylindrical spool or reel body made of plastics material and having apertures passing through the spool body is provided for holding a plaster bandage in rollform. The outwardly facing surface of the spool body is designed to be rough and each of the apertures is spanned by a web extending in the longitudinal direction of the spool body. Each web may have longitudinally extending ridges.

6 Claims, 2 Drawing Figures

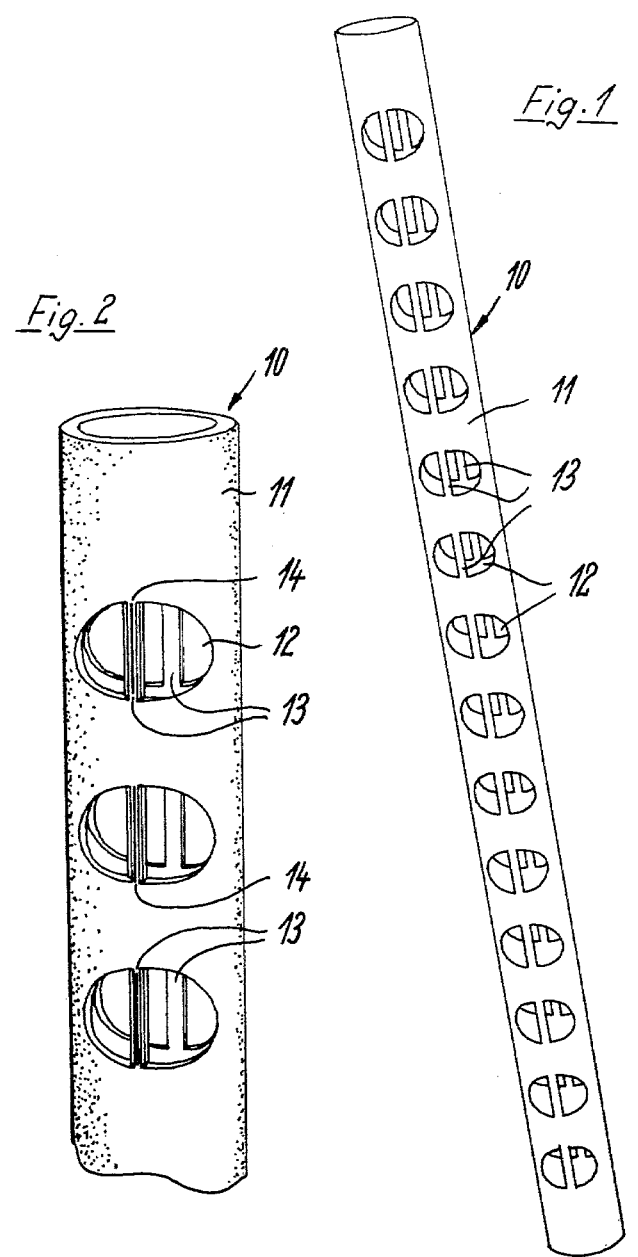

SPOOL BODY FOR HOLDING A PLASTER BANDAGE

The present invention relates to a cylindrical spool or reel body of plastics material for receiving a plaster of Paris bandage in roll form and having apertures passing through the spool body.

When unwinding plaster bandages in order to make a plaster dressing or cast, the spool body with the plaster bandage is guided by hand around the part of the body to be plastered. Spool or reel bodies made of plastics material are known which have either a cruciform cross-section or a circular cross-section, in which case the circular section may have apertures of varying sizes. Moreover, cardboard or pasteboard spool bodies are known which, however, have the disadvantage that in particular already immersed plaster bandages soften the spool body, so that plastics spool bodies have greater stability per se. However, in the case of the latter it has proven to be a disadvantage that the plaster bandage slips relative to the spool body and has practically no secure hold on such spool bodies. This makes rapid and satisfactory handling more difficult which, however, is an unalterable prerequisite for the application of a satisfactory plaster cast or dressing.

An object of the present invention is the provision of a spool or reel body which makes possible secure fixing of the plaster bandage on the spool body and, in particular, prevents the lateral slipping of the spool body during application of the plaster bandage for the purpose of making a plaster cast.

To achieve this object it is proposed according to the present invention, in the case of the spool body described in detail above, that the outwardly facing surface of the spool body is designed to be rough and each of the apertures is spanned by a web extending in the longitudinal direction of the spool body.

The advantage is thereby attained that the plaster of Paris bandage is satisfactorily secured on the spool body in longitudinal direction and even in transverse direction is so guided that, when being unwound, the plaster bandage cannot slip sideways from the spool body. The plaster bandage is supported by the webs in the apertures so that it does not protrude into the interior of the spool body either when being wound on or when being unwound, but is fixed by the webs and the apertures in peripheral direction and longitudinal direction in such a way that the plaster bandage cannot shift, particularly when being unwound. Furthermore, the webs exclude the danger that material will drop through the apertures, which are chosen to have relatively large area, into the spool upon being unwound, or that the material will be caught in the apertures and will impede the unwinding operation.

Advantageously, each web has longitudinally extending ridges or ribs. In this way the plaster bandage receives additional hold, particularly in peripheral direction. In spite of this measure, the advantage achieved according to the invention is retained that the plaster bandage does not become hooked in the apertures, something which would impede separation of the spool body from the end of the plaster banadage. Therefore, because of the webs it is possible to unwind the plaster bandage substantially without obstruction and resistance.

Preferably, the ridges provided on the webs are in alignment with the surface of the spool body, so that the latter has no projecting parts which could deform the plaster bandage or could become hooked up therewith. This could lead to damage to the plaster bandage. Moreover, projecting ridges could result in injury to the plasterer.

In order to fix the plaster bandage uniformly over the entire circumference and to impart a corresponding hold thereto, it is possible to provide two rows of diametrically opposite apertures.

Preferably, the apertures are designed as oblong holes or slots extending in the peripheral direction of the spool body. The action of the webs and ridges for the fixing in peripheral direction is thereby improved.

The spool or reel body advantageously consists of polypropylene which makes possible environmentally acceptable disposal, since during combustion only carbon dioxide and water are given off. Moreover, polypropylene is particularly suitable for providing uniform surface roughness.

This object and other objects and advantages of the invention will appear more clearly from the following specification in connection with the accompanying drawings, in which:

FIG. 1 is a perspective view which illustrates the spool body according to the invention.

FIG. 2 is a detail view which shows an end portion of the spool body greatly enlarged in conformity with the present invention.

Referring now to the drawings in detail, a cylindrical spool or reel body 10 is designed to be of tubular shape with circular cross-section and consists of polypropylene. The outwardly facing surface 11 of the spool body 10 is designed to be uniformly rough, the entire outer surface being provided with very finely spaced elevations and indentations. The degree of roughness corresponds approximately to that of extremely fine abrasive cloth. The inwardly facing surface of the spool body 10 may be of smooth design.

The length of the spool body is preferably matched to the sheet width of the plaster bandage. Lengths of 200 mm are customary. The outer diameter of the spool body 10 may be between 12 and 15 mm.

In the illustrated example of embodiment, the spool body 10 has two longitudinal rows of apertures 12 which are situated diametrically opposite one another. The apertures 12 are designed as oblong holes extending in the peripheral direction of the spool body 10. However, they may also be in the shape of a rhombus or otherwise shaped.

Each aperture 12 is spanned by a web 13 extending in the longitudinal direction of the spool body 10. Preferably, each web 13 has at least one longitudinally extending ridge 14, the web 13 provided with the ridge 14 ensuring a better hold of the plaster bandage in peripheral direction. The ridges 14 are in alignment with the surface 11 of the spool body 10. In this way, despite the surface roughness, the spool body 10 has a continuous cylindrical surface without projections or the like, which is achieved by incorporating the fixing elements for the plaster bandage in longitudinal and transverse direction into the wall of the spool body.

It is, of course, to be understood that the present invention is, by no means, limited to the specific showing in the drawings, but also comprises any modifications within the scope of the appended claims.

What we claim is:

1. A cylindrical spool or reel body made of plastics material for receiving a plaster of Paris bandage in roll form and having apertures passing through said spool body, the improvement in combination therewith comprising: an outwardly facing surface of said spool body made uniformly rough, and a web that spans each of said apertures, said web extending in the longitudinal direction of said spool body to assure a better hold of said bandage in peripheral direction thereof.

2. A spool body in combination according to claim 1, in which each of said webs has longitudinally extending ridges thereon.

3. A spool body in combination according to claim 1, in which each of said webs has longitudinally extending ridges and each of said ridges is in alilgnment with said outwardly facing uniformly roghened surface of said spool body.

4. A cylindrical spool or reel body made of plastics material for receiving a plaster of Paris bandage in roll form and having apertures passing through said spool body, the improvement in combination therewith comprising: an outwardly facing surface of said spool body made uniformly rough, a web which spans each of said apertures and extending in the longitudinal direction of said spool body, longitudinally extending ridges provided on each of said webs, each of said ridges being in alignment with said outwardly facing uniformly rough surface of said spool body, and two rows of said apertures being provided diametrically opposite one another.

5. A spool body in combination according to claim 4, in which said apertures are oblong holes extending in a peripheral direction of said spool body.

6. A spool body in combination according to claim 5, in which said spool body consists of polypropylene.

* * * * *